United States Patent [19]
Kopf

[11] 3,972,229
[45] Aug. 3, 1976

[54] HARDNESS TESTING PROBE ASSEMBLY

[75] Inventor: Rowland J. Kopf, Southington, Conn.

[73] Assignees: Rowland J. Kopf; Madeleine E. DiSantis, both of Elmwood, Conn.

[22] Filed: Nov. 11, 1974

[21] Appl. No.: 522,475

Related U.S. Application Data

[63] Continuation of Ser. No. 410,958, Oct. 29, 1973, Pat. No. 3,894,426.

[52] U.S. Cl. ............................................ 73/85
[51] Int. Cl.² .................................... G01N 3/40
[58] Field of Search ............ 73/81, 82, 83, 84, 85; 227/9, 10, 11, 54

[56] References Cited
UNITED STATES PATENTS
3,172,118  3/1965  Caro et al. ........................ 227/10

FOREIGN PATENTS OR APPLICATIONS
744,822  2/1956  United Kingdom ................ 227/10

Primary Examiner—Jerry W. Myracle
Attorney, Agent, or Firm—Baldwin, Egan, Walling & Fetzer

[57] ABSTRACT

A method is presented for making a penetration test of a homogeneous ceramic material which includes driving a cylindrical hardened steel probe pin of a predetermined configuration into the material to be tested. At the beginning of the test, the pin is snugly assembled in an enclosing tubular cylinder with a flattened end of the pin in registration with one end of the cylinder. After the pin is driven into the material to be tested by use of a closely controlled powder charge in a suitable gun, while holding the tubular cylinder, one may accurately measure the penetration where the flat end of the pin has penetrated the surrounding cylindrical tube. The novel probe pin assembly includes the probe pin assembled in an embracing tube member.

1 Claim, 9 Drawing Figures

HARDNESS TESTING PROBE ASSEMBLY

This is a continuation of application Ser. No. 410,958, filed Oct. 29, 1973, now U.S. Pat. No. 3,894,426.

BACKGROUND OF THE INVENTION

There has long been a need for a simple and reasonably accurate method for determining the compressive strength of homogeneous ceramic material such as masonry bricks of various hardness, concrete blocks, also for the mortar which bonds the bricks and blocks together, and other homogeneous ceramic materials. The present invention utilizes a novel probe pin assembly which may be quickly inserted in the muzzle end of a powder actuated tool, after which the powder charge is exploded driving the probe pin into the material to be tested and the probe pin assembly is so constructed that a very accurate measurement may be made of the penetration of the nose of the pin into the homogeneous ceramic material. This measurement of penetration may be used directly to indicate which of the tested materials are satisfactory and which are unsatisfactory, or the penetration data may be calibrated to provide a graphic chart.

An object of the present invention is to provide a method for making a penetration test of a homogeneous ceramic material by driving a cylindrical hardened steel probe pin into the material to be tested by use of a powder actuated gun.

Another object of the present invention is to provide a probe pin assembly for use in the above mentioned method, the same consisting of a metal cylindrical tube having its ends cut off at right angles to the axis of the cylindrical tube, and with a generally cylindrical probe pin of hardened steel having a driving fit inside of the tube and the driving end of the pin having a flat surface at right angles to its cylindrical axis. In the use of this assembly, the pin is driven into the test material relative to the surrounding tube which provides a convenient and easy way to make a very accurate measurement of the depth of penetration of the pin.

Other objects and advantages of this invention will be apparent from the accompanying drawings and description and the essential features thereof will be set forth in the appended claims.

Figure 1:
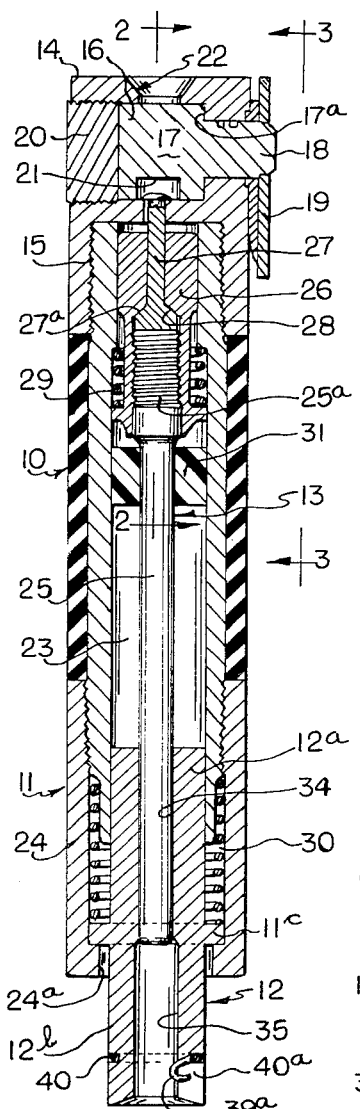
FIG. 1 is a central sectional view through a powder actuated tool or gun which may be used in one embodiment of this invention.
Figure 4:
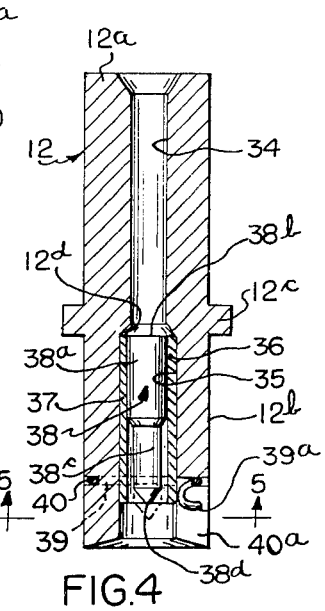
FIG. 4 is an enlarged sectional view of the muzzle bushing assembly seen at the lower part of FIG. 1 taken in section along line 4—4 of FIG. 5.
Figure 6:
Figure 7:
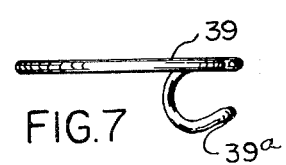
Figure 8A:
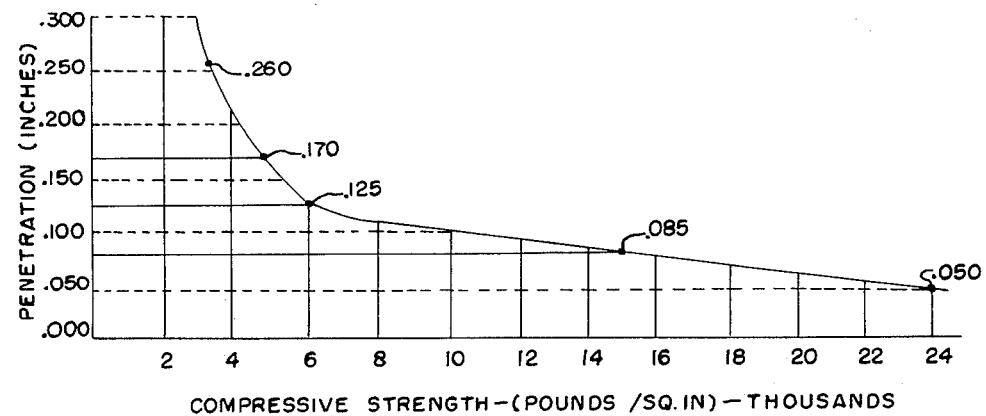
Figure 8B:
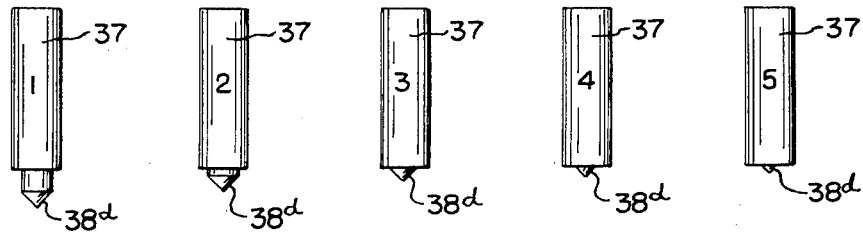

FIGS. 6 and 7 are respectively a plan view and an elevational view of a spring seen near the bottom of FIGS. 1 and 4, the same being utilized to hold the probe pin assembly in position before firing the gun; while FIG. 8A is a graph constructed from data obtained in the testing of five different samples of homogeneous ceramic material and FIG. 8B are side elevations of the probe pin assembly as it appears after completing the tests of the five different materials as plotted in FIG. 8A.

The method of this invention will be explained in connection with a powder-actuated tool as described and claimed in U.S. Pat. No. 3,534,895, granted Oct. 20, 1970 to Robert W. Henning, although it is to be understood that other tools might be adapted for carrying out the method of this invention. This gun will be sufficiently described herein so that one may understand the present invention and further information regarding the gun, if necessary, may be obtained from the above mentioned patent.

The tool comprises generally a housing assembly 10, a barrel assembly 11 attached to the housing assembly, a muzzle bushing assembly 12 operatively connected for relative movement with respect to the barrel assembly, and a piston assembly 13 mounted within the barrel means for relative movement therein.

The housing assembly 10 includes a housing member 14, the forward end of which is provided with an internally threaded counterbore 15 having an axis which extends in the direction of the axis of the tool. A second counterbore 16 is provided in the housing member 14 with its axis extending in a direction perpendicular to the axis of the tool. A cartridge receiving drum 17 is rotatably mounted within the counterbore 16 and the same has an extension of reduced diameter 18 to which an operating handle 19 is connected. A plug 20 is provided with a threaded engagement with the upper portion of the counterbore 16 to confine the drum 17 between the plug 20 and the shoulder 17a between the portions 17 and 18.

Figure 2:
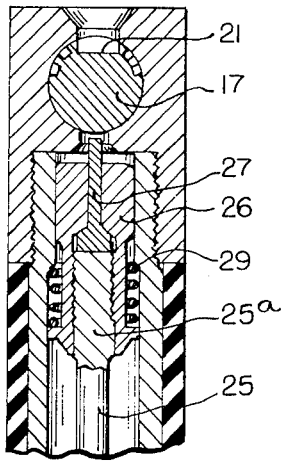
FIG. 2 is a fragmental sectional view taken along the line 2—2 of FIG. 1 showing a loading position for inserting a cartridge of caseless ammunition into the tool preparatory to firing.
Figure 3:
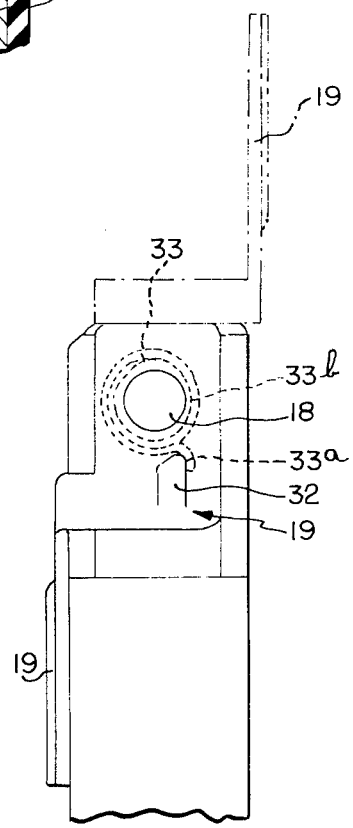
FIG. 3 is a fragmental side elevation taken along the line 3—3 of FIG. 1 illustrating the manipulation of a handle of the tool associated with the loading and firing of the powder actuated gun.

A cartridge receiving chamber 21 is provided in the drum 17 and when the handle 19 is in the full line position of FIG. 3, the chamber 21 is in firing position as shown in FIG. 1. When the handle 19 is in the dotted line position of FIG. 3, then the chamber 21 is in loading position as shown in FIG. 2 in communication with the loading port 22.

The barrel assembly 11 includes a barrel member 23 having its upper end threaded into the counterbore 15 of the housing member 14 and having its lower end threadedly secured in the cap member 24.

The piston assembly 13 includes a piston rod 25 having a thread 25a at its upper end where it is secured to the piston 26. A firing pin 27 extends axially through a bore in the piston and is held in its outer position by a head 27a which abuts a shoulder 28. A spring 29 provides a slight bias of the piston and piston rod downwardly as seen in FIG. 1.

The muzzle bushing assembly 12 is a modification which comprises an upper portion 12a slidably received inside of the barrel 23 unitary wih a lower portion 12b which extends outwardly through the cap 24. An annular flange 12c holds the muzzle bushing captured in the cap 24. A spring 30 urges the muzzle downwardly with the annular flange 12c against the inwardly extending collar portion 24a of the cap.

A cylindrical buffer member 31 is mounted with a frictional fit on the piston rod 25 below the threaded connection 25a. This buffer member may be of any suitable material such as Nylon, polyurethane or other elastomeric materials and its purpose is to prevent damage to the tool in the event of an overdrive of the piston. In such a case, the buffer member 31 will be driven against the flat upper surface of the muzzle bushing portion 12a where the excess energy is absorbed to prevent metal to metal contact of the parts.

As seen in FIG. 3, a portion of the handle 19 is bent inwardly to form a spring abutment surface 32. A spiral spring 33, shown in dotted lines in FIG. 3, is mounted in the space between the handle 19 and the housing member 14 and has one of its ends 33a abutting against the surface 32 and its other end 33b turned inwardly toward the housing portion 14 and mounted in a stop cavity therein to prevent movement of the spring. The purpose of this spring is to serve as a safety device if a cartridge is in chamber 21 in firing position and the operator releases the handle 19 when it is in the corresponding position in FIG. 3 before striking the end of the tool to fire the cartridge. If the operator releases his grip on the handle, the spring 33 will turn the chamber 21 several degrees out of registration with the firing pin 27.

The modification of the above described tool for use in the present invention will now be described. The muzzle bushing assembly 12 has a central bore 34 through the portion 12a of a size to snugly receive the piston rod 25. This bore extends down to the level of the annular flange 12c. Below that point, a larger concentric bore 35 is provided from that point downwardly as clearly seen in FIG. 4. This provides a chamber for receiving the probe pin assembly 36 which comprises a metal cylindrical tube 37 which is open at both ends and cut off normal to the axis of the tube at each end. Snugly fitting in this tube is a probe pin 38 which has an upper portion 38a which preferably has a knurled surface and is force fit into the tube 37 with its flat end 38b presented upwardly and carefully aligned with the squared off upper end of the tube 37. The lower half of the pin as seen at 38c is of lesser diameter, leaving preferably a clearance of about 1/32 of an inch inside the tube 37. This nose portion terminates in a cone shape penetration nose 38d which preferably has an included angle of approximately 90°. When the parts are first assembled, the point of the nose portion 38d is at the level of the squared off bottom portion of tube 37.

In one successful embodiment of this tool, the tube 37 had an outside diameter between 3/8 inches to 23/64 inches and an inside diameter which at the same time was the outside diameter of the probe portion 38a of 5/16 inches. The smaller diameter nose portion of the probe pin 38c in this embodiment was 1/4 inch diameter. The total length of the probe pin assembly was 1 1/8 inches of which about one-half embraced the upper portion 38a of the probe pin and the lower half surrounded the smaller diameter portion 38c.

Figure 5:
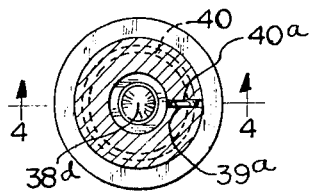
FIG. 5 is a sectional view of the same taken along the line 5—5 of FIG. 4.

Means is provided for holding the probe pin assembly 36 in the bore 35 of the muzzle bushing assembly until the gun is fired. One suitable form of such a device is shown in FIGS. 6 and 7. This comprises a piece of spring wire of generally circular shape 39 lying in a plane and having an end portion 39a bent out of this plane and radially inwardly from the point 39b as shown in FIGS. 1 and 4. The portion 39 is held by its spring action in an annular groove 40 which extends completely around the outer periphery of the bushing portion 12b at a height a little above the lower end of the tube 37 as it is positioned in full lines in FIG. 4. The portion 39a then enters a radially extending milled slot 40a as shown in FIGS. 1, 4 and 5. Before the tube is pushed into the bore 35, the portion 39a of the spring extends slightly into the bore 35 as clearly shown in FIG. 1. This portion 39a then exerts a radially inward pressure against the lower end of the tube 37 when the parts are completely assembled as shown in FIG. 4. Other arrangements might be provided to serve the same function.

The caseless ammunition used in the above described tool is a pellet of compressed ball powder. One such pellet is about 1/8 inch thick and 20 to 21/64 in diameter with a small depression on one side of the pellet in the center. In a well known manner, a drop of primer solution is provided in the central depression, such as fulminate of mercury or a proprietary material. Such a pellet when placed in the chamber 21 has the primer spot presented toward the firing pin 27 when in the position of FIG. 1.

In operation, the probe pin assembly is provided to the operator in the already assembly position of the parts as shown in full line in FIG. 4. The operator then inserts this probe pin assembly into the bore 35 of the muzzle bushing member and pushes it up firmly against a shoulder 12d at about the level of the annular flange 12c. At this time, the piston rod 25 is in the position shown in FIG. 1 with its lower end against the surface 38b of the probe pin. With the handle 19 in the dotted line position of FIG. 3, a powder pellet is placed in the chamber 21 which is then in the position shown in FIG. 2. The handle 19 is then rotated to the full line position of FIG. 3 which presents the powder pellet in the chamber 21 in position registering with the firing pin as shown in FIG. 1. Holding the handle 19 firmly in the position of FIG. 3, the operator places the lower portion 12b of the muzzle bushing against the homogeneous ceramic material to be tested. The operator then strikes the upper end of the tool as seen in FIG. 1 a sharp blow as with a hammer which explodes the powder pellet in the chamber 21 as described in the above mentioned Henning patent. The piston rod 25 moves downwardly at first pushing the probe pin assembly downward from the position seen in FIG. 4 until the lower end of tube 37 engages the surface of the material being tested. Further movement of the piston rod 25 then drives the probe pin 38 downwardly to the dot-dash line position of FIG. 4 penetrating the material being tested. The probe pin assembly is then removed from the muzzle bushing and the operator can then make a very precise measurement of the distance A indicated in FIG. 4 which will indicate how much the nose 38d of the probe pin has penetrated the material being tested. The arrangement of the parts is such that a very exact measurement may be made at this point.

The operator may use the depth of penetration as measured at A in testing other bricks and blocks to determine whether they are of uniform compressive strength or whether they vary up or down. However, the operator may use a chart such as shown in FIG. 8A to aid him in evaluating different samples. One series of tests were run wherein No. 1 was a cement block, No. 2 was a mortar joint between masonry blocks, No. 3 was a soft, sand molded red brick, No. 4 was a medium hard brick, and No. 5 was a much harder brick. Each of the test specimens was then checked for compressive strength in accordance with A.S.T.M. standard method C 67-66. With the first specimen, the probe pin penetration was 0.260 inches and the compressive strength was tested at 3500 pounds per square inch. The second specimen showed a penetration of the probe pin of 0.170 inches and the compressive strength tested 5000 pounds per square inch. The third specimen showed a penetration of 0.125 inches and a compressive strength of 5820 pounds per square inch. The fourth specimen showed a probe pin penetration of 0.085 inches and a compressive strength of 15,280 pounds per square inch. The fifth specimen showed a pentration of 0.050 inches and a compressive strength of 24,160 pounds per square inch. FIG. 8B shows the physical appearance of the probe pin assembly after the nose of the pin was driven into the samples as tested in the numbers running from 1 to 5 as above described.

For accurate results, it is recommended that about three probes might be driven into a given specimen to obtain an average value.

What is claimed is:

1. A probe pin assembly for making a penetration test of a homogeneous ceramic material using a powder actuated gun to drive said probe pin assembly, said probe pin assembly consisting of a metal cylinder tube having its ends cut off at right angles to the axis of said cylindrical tube, a generally cylindrical probe pin of hardened steel having a driving fit inside of said tube, the driving end of said pin having a flat surface at right angles to its cylindrical axis exactly at the level of one end of said tube, the other end of said pin having a cone shape penetration nose, and the overall length of said pin being exactly the same length as said tube, whereby after driving said probe pin into said ceramic material, the penetration can be measured by measuring the distance said flat surface has been driven into said tube.

* * * * *